United States Patent [19]
Campbell

[11] Patent Number: 5,476,454
[45] Date of Patent: Dec. 19, 1995

[54] BALLOON CATHETER LOCK ADAPTOR FOR USE WITH A RESTERILIZATION SYSTEM

[75] Inventor: James L. Campbell, Plymouth, Minn.

[73] Assignee: Minntech Corporation, Minneapolis, Minn.

[21] Appl. No.: 97,891

[22] Filed: Jul. 28, 1993

Related U.S. Application Data

[63] Continuation-in-part of Ser. No. 835,729, Feb. 11, 1992, Pat. No. 5,310,524.

[51] Int. Cl.[6] ................................................. A61M 25/00
[52] U.S. Cl. ........................... 604/283; 604/96; 604/905; 134/166 C
[58] Field of Search ................................ 604/96, 97, 102, 604/103, 283, 905; 134/22.12, 22.18, 166 R, 166 C, 170; 206/363; 422/292, 295, 297

[56] References Cited

U.S. PATENT DOCUMENTS

| | | | |
|---|---|---|---|
| 4,721,123 | 1/1988 | Cosentino et al. | |
| 5,125,915 | 6/1992 | Berry et al. | 604/283 |
| 5,154,725 | 10/1992 | Leopold | 606/194 |
| 5,279,317 | 1/1994 | Bowman et al. | 134/166 |
| 5,279,597 | 1/1994 | Dassa et al. | 604/283 |
| 5,338,314 | 8/1994 | Ryan | 604/284 |

*Primary Examiner*—Corrine M. Maglione
*Attorney, Agent, or Firm*—Cushman, Darby & Cushman

[57] ABSTRACT

An adaptor for coupling rapid exchange-type catheters to a catheter re-sterilizing system. Specifically, the adaptor fluidly couples the guidewire lumen of a rapid exchange-type catheter to a source of sterilant so that the sterilant may be positively directed to and through the guidewire lumen, thereby allowing the catheter to be properly "reprocessed" or sterilized for reuse.

12 Claims, 2 Drawing Sheets

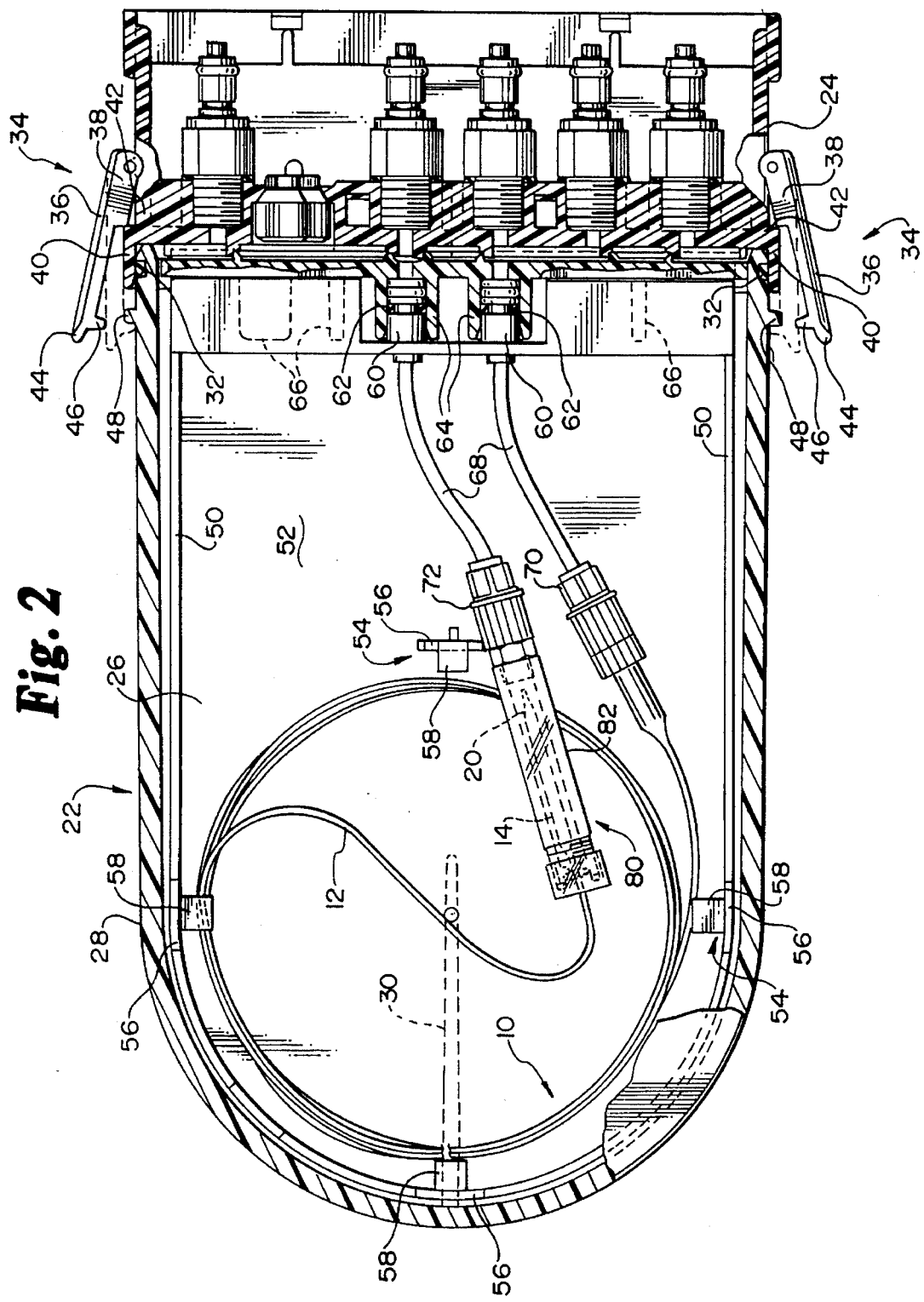

BALLOON CATHETER LOCK ADAPTOR FOR USE WITH A RESTERILIZATION SYSTEM

This application is a continuation-in-part of application No. 07/835,729 filed Feb. 11, 1992 now U.S. Pat. No. 5,310,524.

BACKGROUND OF THE INVENTION

1. Field of the Invention

The present invention relates to catheter reprocessing systems and, more particularly, to an adaptor for reprocessing a rapid exchange-type catheter in an angioplasty catheter reprocessing system.

2. Description of the Related Art

Percutaneous transluminal angioplasty has become a common and popular method for treating arteries obstructed by plaque. The cost of the various types of catheters used in such procedures represents a significant portion of the overall cost of the procedure. It has therefore been proposed to reprocess and reuse catheters to help control the spiraling cost of the surgical procedure itself.

Manual reprocessing of catheters has provided one means for reprocessing and reusing catheters. However manual reprocessing is prone to human error and the sterility which is critical to a successful operation cannot always be guaranteed. Similarly, manual systems cannot guarantee the integrity of the catheter following reprocessing.

Commonly owned U.S. Pat. No. 4,721,123, the disclosure of which is incorporated herein by this reference, overcomes many of the problems associated with manual reprocessing by providing an automated reprocessing system.

Commonly owned application No. 07/835,729, the disclosure of which is incorporated herein by this reference, relates to another reprocessing and sterilizing system which represents a significant advance in the art by allowing re-sterilization of catheters in minutes and by enabling the use of a unique catheter sterilizing cassette that permits storage of sterilized catheters for periods of one week to one month without breaks in sterility. That catheter reprocessing system is designed for conventional over the wire-type catheters.

More particularly, over the wire-type catheters have a bifurcated proximal end with the balloon inflation port and the guidewire lumen port each having luer lock-type ends. The used catheter to be reprocessed is inserted into a reprocessing cassette, and the two luer lock ends are attached respectively to the reprocessing machine via a balloon inflation fill and drain valve and a guidewire lumen fill and drain valve of the cassette. Through a series of steps, the catheter's guidewire lumen and balloon and inflation lumen are flushed and sterilized with heated sterilant.

That reprocessing system is not, however, designed to accommodate the more recently developed and increasingly popular rapid exchange-type catheters. Indeed, in rapid exchange catheters, the guidewire lumen proximal port does not have a luer lock end. It is simply a hole in the side of the catheter body. Since it is not possible to couple the guidewire lumen of rapid exchange-type catheters in the cassette of the '729 application structure, it is not possible to actively flush the guidewire lumen with sterilant.

SUMMARY OF THE INVENTION

It is an object of the invention to provide an adaptor so that rapid exchange-type catheters can be reprocessed in particular in a reprocessing system of the type disclosed in the '729 application. The adaptor of the invention permits the guidewire lumen of the rapid exchange-type catheter to be fluidly coupled to a source of sterilant so that the sterilant may be positively directed to and through the guidewire lumen of the rapid exchange-type catheter thereby to allow the catheter to be properly "reprocessed" or sterilized for reuse.

The foregoing object is achieved by providing an adaptor which sealingly engages an exterior surface of the catheter proximal to the balloon portion thereof but distal to the proximal guidewire port, and encloses the balloon portion of the catheter with a tubular main body which extends beyond the distal opening of the guidewire lumen of the catheter. The adaptor terminates in a luer-lock type coupling which can be matingly coupled directly or indirectly to the luer-lock type connector provided on the reprocessing system for flushing the guidewire lumen. Sterilant from the reprocessing system will thus be directed to the distal tip of the monorail catheter and through the guidewire lumen thereby insuring that the guidewire lumen will be sterilized during the reprocessing procedure.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 2 is a sectional view taken along line 2—2 in FIG. 1, showing internal details of the cartridge with the adaptor of the invention therewithin;

DETAILED DESCRIPTION OF THE PRESENTLY PREFERRED EXEMPLARY EMBODIMENTS

Figure 1:
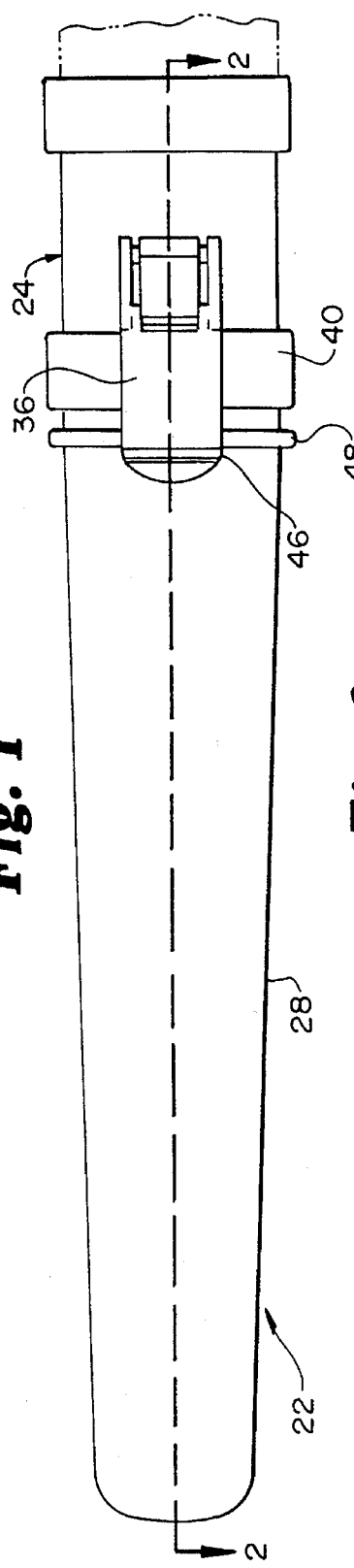
FIG. 1 is a side elevational view of a catheter cleaning cartridge assembly.

An exemplary rapid exchange-type balloon tipped catheter to be reprocessed and sterilized is shown in FIG. 2. The catheter 10 is generally cylindrical and includes an elongated tubular member 12 and a balloon 14.

The guidewire lumen 16 is relatively short and opens proximally of the balloon 14 at a proximal port (not shown in particular), generally 10 to 30 centimeters from the distal tip 20 of the catheter 10. An inflation lumen 18 extends between the proximal end of the catheter and the balloon at its tip. Known rapid exchange-type catheters provide side-by-side, parallel, guidewire and inflation lumens distally, while the proximal end of the catheter is dedicated to balloon inflation. It is to be appreciated, however, that the internal lumen configuration is not particularly pertinent to the present invention.

Referring to FIG. 2, the reprocessing and sterilizing cassette 22 in accordance with the invention includes a cassette door 24, a disposable tray 26 and a cartridge 28.

The cartridge 28 may be molded as a one piece unit or may be formed in two or more parts which are coupled together so as to define a fluid tight compartment therewithin. The cartridge 28 is generally U-shaped in horizontal cross section so that the closed end of the cartridge is rounded as in a semicircle to correspond to the shape of the coiled catheter which is placed therewithin, thereby maximizing efficient use of space. One or more reinforcing ribs 30 may be integrally molded with the upper and lower walls of the cartridge or another reinforcement may be provided as necessary or desirable.

The cassette door 24 is generally rectangular in vertical cross-section but with the corners of the rectangle rounded. Thus, the door is shaped and configured to snugly engage the open end of the cartridge. In the illustrated embodiment, the door 24 is sized to receive the open end of the cartridge 28. A seal, such as an O-ring 32, is provided between the door 24 and the cartridge 28 to ensure a tight, hermetically sealed fit. Advantageously, locking latch assemblies or other suitable coupling means 34 are also provided to hold the door 24 on the cartridge 28 during and after reprocessing. In the illustrated embodiment, the latch assembly 34 includes an elongated latch member 36 pivotally coupled to the door 24. The latch member has a shoulder portion 38 having a length such that when the latch member is pivoted to a closed, locking position (phantom lines), the end of the shoulder is closely adjacent or even engaging the peripheral lip 40 of the door 24. To that end, an axially extending rim (not shown) may be provided at the shoulder end 42 of the lip 40 to provide for a snap engagement and frictional retention between the latch member 36 and lip 40. The distal end 44 of the latch member 36 has a projecting flange 46 for engaging a locking flange 48 on the cartridge 28 to retain the cartridge and door in a coupled disposition.

A tray 26 is provided which is a preferably unitary, generally U-shaped piece that is preferably transparent, and may be molded from any resilient synthetic material such as PVC (polyvinylchloride), polyolfin or like materials. The tray is molded to have peripheral side walls 50 thereby defining a solution receiving cavity 52.

In the illustrated embodiment, catheter holding units 54 are provided at spaced locations within the cavity about the tray. As can be seen, the catheter holding units 54 each include an upstanding portion 56 and a horizontal flange or lip 58 which contain the catheter 10 in a predetermined, generally circular segment of the tray 26. The tray 26 is further provided with a plurality of male couplers 60, each including O-ring seal(s) 62, which sealingly engage female connectors 64 provided on the cassette door 24. The male couplers 60 on the tray 26 are in turn coupled to sterilant tubes 68 which terminate at their distal ends in luer-type connectors 70,72 although other types of connectors may be provided as desired. Projecting from the cassette door are flange elements 66 which facilitate alignment and coupling of the cassette door to the tray.

As discussed more fully below, connector 70 is adapted to engage in a fluid tight manner the proximal luer-type connector (not shown in detail) of the balloon inflation passage. Connector 72 is provided to engage in a secure, fluid tight manner the luer-type connector provided on the distal end of the adaptor 80 of the invention which, as is also described more fully below, is mounted to the distal, balloon tipped end of the catheter 10. In practice, the tray is mounted to the canister door so that the male couplers 60 are sealingly received in the female connectors 64 of the cassette door 24 and the tray and cassette door combination is then attached to the cartridge with the tray inserted into the cartridge. As can be seen, the tray and canister are correspondingly shaped to provide a complimentarily, interfitting structure. The latch assemblies are then snapped into their locking position.

Figure 3:
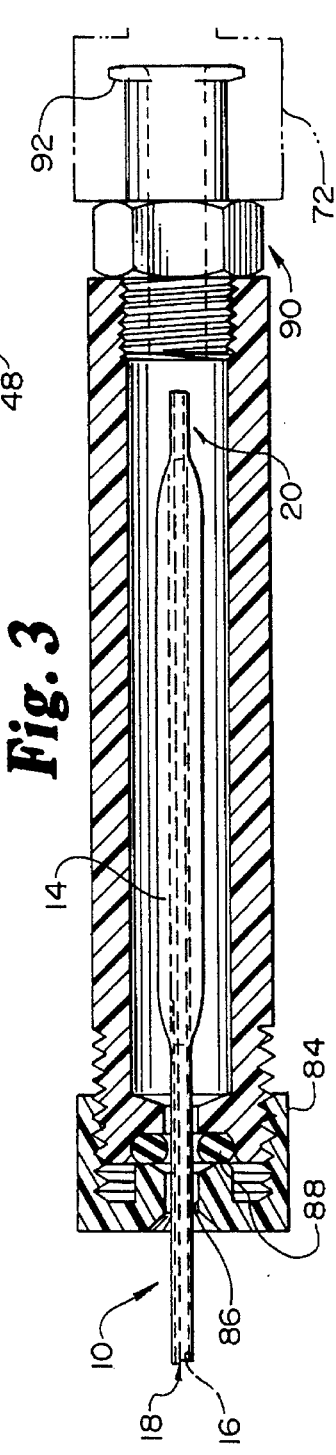
FIG. 3 is a sectional view of the inventive adaptor taken along the longitudinal axis thereof in a non-sealed state and showing the catheter therewithin.
Figure 4:
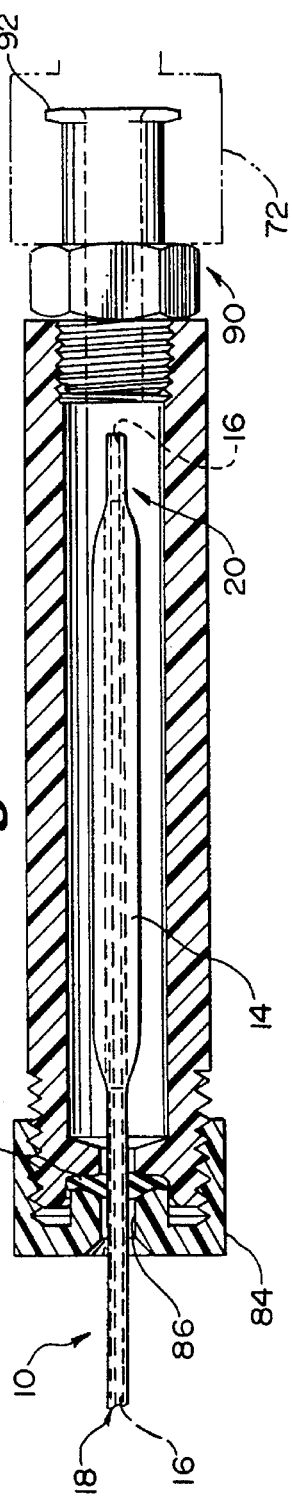
FIG. 4 is a view similar to that of FIG. 3 showing the adaptor in a sealed state, coupled to the exterior of the catheter.

With reference to FIGS. 3 and 4, the adaptor of the invention will now be described in greater detail.

As noted above rapid exchange-type catheters are distinct from other angioplasty catheters in that a luer lock type connector is absent from the guidewire lumen. Thus, an adaptor 80 in accordance with the invention can be advantageously mounted in surrounding relation to the balloon 14 of the rapid exchange-type angioplasty catheter 10 to place the guidewire lumen in direct flow communication with a source of sterilant. The adaptor 80 includes a housing 82 which is preferably of cylindrical shape with a circular transverse cross-section and of a length suitable to receive the entire balloon 14 of the associated balloon catheter 10. As can be appreciated, it is desirable for the length of the adaptor to exceed the length the balloon on the tip of the catheter so that fluid tight securement of the proximal end of the adaptor will not close off the balloon and thus hamper sterilization of that segment of the catheter via sterilant delivery to the balloon inflation lumen.

Although it is envisioned that a variety of sealing couplings between the adaptor and the catheter may be provided, in the illustrated embodiment, a cap 84 having a central bore 86 is mounted to the proximal end of the cylindrical housing 82 of the adaptor and a distortable O-ring type sealing element 88 is mounted therebetween. Thus, as can be seen from a comparison of FIGS. 3 and 4, engagement of the cap 84 with the housing and displacement so as to advance the cap onto the housing compresses and displaces the O-ring 88, thereby decreasing the diameter of the center of the O-ring and thereby sealingly engaging the catheter 10 which has been disposed therethrough. Although a threaded attachment of the cap to the end of the housing has been illustrated and is preferred because it allows a continuous decrease in size of the passage through the O-ring as the cap is tightened, it is to be understood that other attachment and displacement means may be provided such as a bayonet-type attachment, if it is determined that a sufficient seal is provided with the compression afforded by the bayonet-type or other displacement mechanism.

In the illustrated embodiment, the distal most end of the housing is provided with a suitable connector 90. Because the illustrated reprocessing system utilizes a luer-type coupling system, in the illustrated embodiment a luer-type configuration having radially projecting "ears" 92 is defined at the distal end of the housing. It should be appreciated that the particular type of connector provided at the distal end of the adaptor body depends upon the reprocessing system and, in particular, the type of coupling with which the adaptor is to be coupled and whether an extension tube having a particular coupling is provided. Thus, it is to be appreciated that connectors other than connectors of the luer-type may be provided if such is required for the particular reprocessing system and/or extension tube being utilized. Furthermore, while the connector 90 is illustrated as threaded to the distal end of the housing, it is to be appreciated that the connector employed may be integrally formed with the distal end of the housing, or coupled thereto in another manner.

With the foregoing assembly, when a rapid exchange-type or other catheter having a distal opening or openings is to be reprocessed in accordance with the invention, the distal tip of the catheter is inserted into the adaptor when the proximal end is in the unsealed disposition shown in FIG. 3. Once the balloon tip has been entirely received within the interior of the adaptor, sealing engagement is effected between the proximal end of the adaptor and the exterior surface of the catheter proximal of the balloon. To accomplish this illustrated embodiment, the cap 84 is displaced on the adaptor body so that the O-ring 88 is distorted to sealingly engage the catheter at a point between the balloon and the proximal guidewire port. Then, the distal end of the adaptor is coupled to the coupling device 72 provided in the reprocessing tray for delivering sterilant to the lumen which is to be flushed and which is in communication with the interior of the adaptor. As an alternative, the adaptor 80 may be coupled to the sterilant delivery tube before the catheter is engaged with the adaptor.

The other sterilant flushing connector 70 is coupled to the balloon inflation lumen at its distal end in the manner disclosed in the '729 application. It should be noted that if no coupling structure is provided at the proximal end of the balloon inflation lumen, then another adaptor in accordance with the present invention may be provided at that end of the catheter and sealingly engaged in a like manner so that the proximal opening is disposed within the inventive adaptor structure.

Once the guidewire lumen and balloon inflation lumen have been fluidly coupled to the reprocessing system and the catheter mounted on the tray in the manner disclosed in the '729 application so as to be coiled in a loop and thereby neatly placed within the tray, the tray which is advantageously already mounted to the cassette door is then inserted into the cartridge and the reprocessing procedure set forth in the '729 application is carried out.

The adaptor is removed from the catheter by releasing the cap seal and axially shifting the catheter out of the adaptor.

Although the invention has been described with reference, in particular, to rapid exchange-type catheters, it is to be understood, as noted above, that the adaptor of the invention can be used to facilitate reprocessing of any catheter which has a lumen or lumens having an axial and/or radial opening or openings, particularly, but not necessarily, at or adjacent an end thereof and which lacks a connector structure. Thus, for example, the adaptor of the invention could be coupled to the proximal end of the catheter where for example the luer adaptor has been removed. Furthermore, while the inventive adaptor is disclosed with reference in particular to the reprocessing system of the '729 application it is to be understood that the inventive adaptor could be utilized to provide a coupling device for any of a variety of automatic or manual reprocessing systems.

Accordingly, while the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. An adaptor for providing flow communication between a source of reprocessing fluid and a lumen of a catheter structure that has a first port and a second port, at least one of which lacks a connector structure, said adaptor comprising:

a main body having a longitudinal axis, a first end, and a second end, said first end and said second end being at longitudinal ends of said main body;

means for coupling the first end of said main body in a fluid tight manner to an exterior surface of the catheter structure between the first port and the second port of the lumen; and means for coupling the second end of said main body to a connector assembly of the source of reprocessing fluid, said means for coupling to a connector assembly including first and second, radially outwardly projecting tab elements for locking engagement with a luer-type connector assembly, whereby when the first end is coupled to the catheter and the second end is coupled to the fluid source, a reprocessing fluid can be delivered to and flushed through the lumen.

2. An adaptor as in claim 1, wherein said means for fluid tight coupling includes a cap mounted to said main body and a deformable O-ring interposed between said main body and said cap so that displacement of said cap toward said main body distorts said O-ring into engagement with the exterior surface the catheter thereby providing said fluid tight coupling.

3. An adaptor as in claim 1, wherein said main body has a circular cross-section.

4. An adaptor in combination with a reprocessing system having a hollow cartridge body having an open end, a tray which is slidably receivable in said hollow cartridge body through said open end, and a cassette door for closing and sealing said open end, at least one of said tray and said cassette door including a connector assembly for coupling to a source of sterilant, said adaptor comprising:

a main body having a longitudinal axis, a first end, and a second end;

means for coupling the first end of said main body in a fluid tight manner to an exterior surface of a catheter structure between a first port and a second port of a lumen thereof; and means for coupling the second end of said main body to said connector assembly, whereby when the first end is coupled to the catheter and the second end is coupled to the fluid source, a reprocessing fluid can be delivered to and flushed through the lumen.

5. The combination of claim 4, wherein said means for fluid tight coupling includes a cap mounted to said main body and a deformable O-ring interposed between said main body and said cap so that displacement of said cap toward said main body distorts said O-ring into engagement with the exterior surface the catheter thereby providing said fluid tight coupling.

6. The combination of claim 4, wherein the connector assembly is a luer-type connector and said means for coupling to the connector assembly includes first and second tab elements for locking engagement with said connector assembly.

7. The combination of claim 4, wherein said first end and said second end are at longitudinal ends of said main body.

8. The combination of claim 4, wherein said main body has a circular cross-section.

9. An adaptor for providing flow communication between a source of reprocessing fluid that has a connector assembly and a lumen of a catheter structure that has a first port and a second port, at least one of which lacks a connector structure, said adaptor comprising:

a housing having a chamber defined therewithin;

means for coupling one portion of the housing in a fluid tight manner to an exterior surface of the catheter structure between the first port and the second port of the lumen, said means for coupling including a cap mounted to said housing and a deformable O-ring interposed between said housing and said cap so that axial displacement of said cap towards the housing distorts said O-ring into engagement with the exterior surface of the catheter thereby providing said fluid tight coupling; and means for connecting another portion of the housing to the connector assembly of the source of reprocessing fluid, walls of said housing intermediate said coupling means and said connecting means being free of fluid inlets and outlets, whereby fluid entering said housing through said connecting means is substantially limited to an outlet flow path defined through the lumen of the catheter, whereby when the coupling means is coupled to the catheter and the connector means is connected to the reprocessing fluid source, a reprocessing fluid can be delivered to and flushed through the lumen.

10. A catheter in combination with an adaptor, the catheter comprising:

a tubular member having a proximal end, a distal end, a balloon element defined adjacent said distal end, an inflation lumen extending therethrough from said balloon element toward said proximal end, and a guidewire lumen extending from a distal port at said distal end to a proximal port proximal to said balloon element but distal to said proximal end, said adaptor providing flow communication between a source of reprocessing fluid and said guidewire lumen of said catheter, said adaptor comprising:

a main body having a longitudinal axis, a first end, and a second end;

means for coupling the first end of said main body in a fluid tight manner to an exterior surface of the catheter structure between the distal port and the proximal port of the lumen, said means for coupling the first end including structure selectively rotatable relative to said main body for selectively displacing a deformable element into fluid-tight engagement with said exterior surface of the catheter structure; and means for connecting the second end of said main body to a connector assembly of the source of reprocessing fluid, walls of said housing intermediate said coupling means and said connecting means being free of fluid inlets and outlets, whereby fluid entering said housing through said connecting means is substantially limited to an outlet flow path defined through the lumen of the catheter, whereby when the first end is coupled to the catheter and the second end is coupled to the fluid source, said balloon element is disposed within said adaptor and a reprocessing fluid can be delivered to and flushed through the lumen.

11. A method of reprocessing a catheter, comprising:

providing a catheter to be reprocessed, the catheter having an exterior surface, a lumen that has a first port and a second port, at least one of which lacks a connector structure, and an inflatable balloon structure provided intermediate said first and second ports;

providing a reprocessing system including a source of sterilant and a connector assembly for providing access to sterilant therewithin;

providing an adaptor for providing flow communication between the source of sterilant and the lumen of the catheter structure, said adaptor comprising:

a main body having a longitudinal axis, a first end, and a second end;

means for coupling the first end of said main body in a fluid tight manner to the exterior surface of the catheter between the first port and the second port of the lumen, said means for coupling the first end including structure selectively rotatable relative to said main body for selectively displacing a deformable element into fluid tight engagement with said exterior surface of the catheter structure; and means for coupling the second end of said main body to the connector assembly of the source of sterilant, inserting one end of the catheter into the adaptor through the first end thereof;

sealingly coupling said first end to the exterior surface of the catheter between the first port and the second port, said step of coupling including rotating said selectively rotatable structure relative to said main body;

coupling the second end of the adaptor to the connector assembly of the source of sterilant; and delivering sterilant to said adaptor and through said lumen.

12. A method as in claim 11, wherein said step of sealingly coupling follows said step of coupling the second end.

* * * * *